US006921808B2

(12) United States Patent
Joergensen et al.

(10) Patent No.: US 6,921,808 B2
(45) Date of Patent: Jul. 26, 2005

(54) PURIFICATION PROCESS FOR LARGE SCALE PRODUCTION OF GC-GLOBULIN, THE GC-GLOBULIN PRODUCED HEREBY, A USE OF GC-GLOBULIN AND A GC-GLOBULIN MEDICINAL PRODUCT

(75) Inventors: Charlotte Svaerke Joergensen, Naestved (DK); Inga Laursen, Hellerup (DK); Gunnar Houen, Virum (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 10/920,503

(22) Filed: Aug. 18, 2004

(65) Prior Publication Data

US 2005/0020816 A1 Jan. 27, 2005

Related U.S. Application Data

(62) Division of application No. 10/217,787, filed on Aug. 13, 2002, now Pat. No. 6,806,355.
(60) Provisional application No. 60/315,124, filed on Aug. 27, 2001.

(30) Foreign Application Priority Data

Aug. 14, 2001 (DK) ........................................ 2001 01217

(51) Int. Cl.[7] .............................................. C07K 14/00
(52) U.S. Cl. ........................ 530/380; 530/414; 530/416
(58) Field of Search ................................. 530/380, 414, 530/416

(56) References Cited

U.S. PATENT DOCUMENTS

5,326,749 A 7/1994 Yamamoto

FOREIGN PATENT DOCUMENTS

| WO | WO 91/15770 A1 | 10/1991 |
| WO | WO 96/40903 A1 | 12/1996 |
| WO | WO 97/28688 A1 | 8/1997 |

OTHER PUBLICATIONS

E. Cohn et al, "Preparation and Properties of Serum and Plasma Proteins. IV. A System for the Separation into Fractions of the Protein and Lipoprotein Components of Biological Tissues and Fluids", J. Am. Chem. Soc., 68:459–475 (Mar., 1946).
N. Cooke et al, "Serum Vitamin D–binding Protein is a Third Member of the Albumin and Alpha Fetoprotein Gene Family", J. Clin. Invest., 76:2420–2424 (Dec., 1985).
B. Dahl et al, "Serum Gc–globulin in the Early Course of Multiple Trauma", Crit. Care Med., 26(2):285–289 (1998).

P. Goldschmidt–Clermont et al, "Proportion of Circulating Gc (Vitamin D–Binding Protein) in Complexed Form: Relation to Clinical Outcome in Fulminant Hepatic Necrosis", Gastroenterology, 94(6):1454–1458 (1988).
F. Wians et al, Immunonephelometric Quantification of Group–Specific Component Protein in Patients with Acute Liver Failure, Liver Transplantation and Surgery, 3(1):28–33 (Jan., 1997).
P. Walsh et al, "'Rocket' Immunoelectrophoresis Assay of Vitamin D–Binding Protein (Gc Globulin) in Human Serum", Clinical Chemistry, 28(8):1781–1783 (1982).
C. Chapuis–Cellier et al, "Interaction of Group–Specific Component (Vitamin D–Binding Protein) with Immobilized Cibacron Blue F3–GA", Biochimica et Biophysica Acta., 709:353–357 (1982).
R. Bouillon et al, "Serum Vitamin D Metabolites and Their Binding Protein in Patients with Liver Cirrhosis", J. Clin. Endocrinol. and Metab., 59(1):86–89 (1984).
H. Cleve et al, "Isolation and Partial Characterizatiion of the Two Principal Inherited Group–Specific Components of Human Serum", J. Exp. Med., 118:711–726 (1963).
F. Schiodt et al, "Admission Levels of Serum Gc–Globulin: Predictive Value in Fulminant Hepatic Failure", Hepatology, 23:713–718 (1996).
F. Schiodt et al, "Serial Measurements of Serum Gc–Globulin in Acetaminophen Intoxication", European Journal of Gastroenterology & Hepatology, 7:635–640 (1995).
F. Schiodt et al, "Reduced Serum Gc–Globulin Concentrations in Patients with Fulminant Hepatic Failure: Association with Multiple Organ Failure", Crit. Care Med., 25(8):1366–1370 (1997).
J. Svasti et al, "Human Group–Specific Component, Changes in Electrtophoretic Mobility Resulting from Vitamin D Binding and from Neuraminidase Digestion", J. Biol. Chem., 253(12):4188–4194 (Jun., 1978).
N. Swamy et al, "Affinity Purification of Human Plasma Vitamin D–Binding Protein", Protein Expression and Purification, 6:185–188 (1995).

(Continued)

Primary Examiner—Karen Cochrane Carlson
Assistant Examiner—Anand Desai
(74) Attorney, Agent, or Firm—Howson and Howson

(57) ABSTRACT

A purification process for large-scale production of Gc-globulin is described. The source of Gc-globulin is preferably a crude plasma fraction but can be any solution, suspension or supernatant containing Gc-globulin, e.g., a milk product, colostrum or a fermentation broth. The Gc-globulin can be plasma-derived or produced by a genetic modified organism. The process includes two key elements: purification by series of ion exchange chromatography steps, and performing at least two virus-reduction steps. A diagnostic method to measure the free Gc-globulin in a patient blood sample, a use of Gc-globulin in medicine and the preparation of a Gc-globulin medicinal product is also provided. The product can be used in therapy for patients with circulatory disorders and complications, i.e., where it is contemplated that patients would benefit from the administration of Gc-globulin.

6 Claims, No Drawings

OTHER PUBLICATIONS

W. Lee et al, "The Extracellular Actin–Scavenger System and Actin Toxicity", N. Engl. J. Med., 326(20):1335–1341 (May, 1992).

W. Lee et al, "Predicting Survival in Fulminant Hepatic Failure Using Serum Gc Protein Concentrations", Hepatology, 21:101–105 (1995).

R. Link et al, "Purification of Human Serum Vitamin D–Binding Protein by 25–Hydroxyvitamin $D_3$–Sepharose Chromatography", Analytical Biochemistry, 157:262–269 (1986).

L. Miribel et al, "Rapid Purification of Native Group–Specific Component (Vitamin D–Binding Protein) by Differential Affinity for Immobilized Triazine Dyes", J. Chromatography, 363:448–455 (1986).

S. Dueland et al, "Uptake and Degradation of Filamentous Actin and Vitamin D–Binding Protein in the Rat", Biochem. J., 274:237–241 (1991).

J. Haddad et al, "25–Hydroxyvitamin D Transport in Human Plasma", J. Biol. Chem., 251(16):4803–4809 (Aug., 1976).

J. Haddad et al, "Actin Affinity Chromatography in the Purification of Human, Avian and Other Mammalian Plasma Proteins Binding Vitamin D and its Metabolites (Gc Globulins)", Biochem. J., 218:805–810 (1984).

H. Van Baelen et al, "Vitamin D–Binding Protein (Gc–Globulin) Binds Actin", J. Biol. Chem., 255(6):2270–2272 (Mar., 1980).

J. Barragry et al, "Plasma Vitamin D–Binding Globulin in Vitamin D Deficiency, Pregnancy and Chronic Liver Disease", Clinica Chimic Acta., 87:359–365 (1978).

R. Bouillon et al, "The Purification and Characterisation of the Human–Serum Binding Protein for the 25–Hydroxycholecalciferol (Transcalciferin)", Eur. J. Biochem., 66:285–291 (1976).

G. Taylor et al, "Purification of Vitamin D Binding Protein from Human Plasma Using High Performance Liquid Chromatography", Clinica Chimica Acta., 155:31–42 (1986).

J.G. Haddad, et al., "Angiopathic consequences of saturating the plasma scavenger system for actin", Proc. Natl. Acad. Sci. USA, Feb. 1990, pp. 1381–1385, vol. 87.

J.G. Haddad, "Plasma Vitamin D–binding Protein (Gc–globulin): Multiple Tasks", J. Steroid Biochem. Molec. Biol., 1995, pp. 579–582, vol. 53, Elsevier Science Ltd., Great Britain.

K.D. Harper, et al., "Vitamin D Binding Protein Sequesters Monomeric Actin in the Circulation of the Rat", J. Clin. Invest., May 1987, pp. 1365–1370, vol. 79, The American Society for Clinical Investigation, Inc.

K. Heide, et al., "Darstellung noch nicht therapeutish angewandter Plasmaproteine", Berlingwerk Mitteilungen, 1964, pp. 161–193, vol. 43.

M. Kawakami, et al., "Turnover of the Plasma Binding Protein for Vitamin D and Its Metabolites in Normal Human Subjects", Journal of Clinical Endocrinology and Metabolism, 1981, pp. 1110–1116, vol. 53, No. 6, The Endocrine Society, USA.

P. Kistler, et al., "Large Scale Production of Human Plasma Fractions", Vox. Sang., 1962, pp. 414–424, vol. 7.

W.M. Lee, et al., "Diminished Serum Gc (Vitamin D–Binding Protein) Levels and Increased Gc:G–Actin Complexes in a Hamster Model of Fulminant Hepatic Necrosis", Hepatology, 1987, pp. 825–830, vol. 7, No. 5, American Association for the Study of Liver Diseases, USA.

W.M. Lee, et al., "Alterations in Gc Levels and Complexing in Septic Shock", Circulatory Shock, 1989, pp. 249–255, vol. 28.

A.R. Torres, et al., "Purification of Gc–2 Globulin from Human Serum by Displacement Chromatography: A Model for the Isolation of Marker Proteins Identified by Two–Dimensional Electrophoresis", Analytical Biochemistry, 1985, pp. 469–476, vol. 144, Academic Press, Inc.

D. Roelcke, et al., "Gc–Darstellung mittels Hydroxylapatit–Säulen–Chromatographie", Blut, 1967, pp. 331–340, 14.

PURIFICATION PROCESS FOR LARGE SCALE PRODUCTION OF GC-GLOBULIN, THE GC-GLOBULIN PRODUCED HEREBY, A USE OF GC-GLOBULIN AND A GC-GLOBULIN MEDICINAL PRODUCT

CROSS-REFERENCE TO RELATED APPLICATIONS

This is a division application of U.S. patent application Ser. No. 10/217,787 filed on Aug. 13, 2002 now patented, U.S. Pat. No. 6,806,355, which claims the benefit of U.S. Provisional Application No. 60/315,124, filed Aug. 27, 2001, and priority of Danish patent application PA 2001 01217, filed Aug. 14, 2001.

BACKGROUND OF THE INVENTION

Gc-globulin (also designated vitamin D-binding protein) is an important plasma protein with a concentration in human plasma of approximately 300–350 mg/l (Haddad, 1995).

The daily synthesis of Gc-globulin has been determined to be 10 mg/kg bodyweight and the exchangeable pool of Gc-globulin has been estimated to be 2.9 g (80 kg bodyweight) (Kawakami et al., 1981). This gives an estimated half-life for Gc-globulin of approximately 2 days. Gc-globulin has a molecular mass of approximately 51 kDa and the complete structure of Gc-globulin has been determined (Cooke and David, 1985).

Gc-globulin is an actin-binding protein (Baelen et al., 1980), and is a part of the plasma actin-scavenging system (Lee and Galbraith, 1992). The plasma actin-scavenging system consists of gelsolin, which dissociates polymeric F-actin to monomeric G-actin subunits and Gc-globulin which sequesters G-actin and removes it from the circulation.

Actin is a cytoskeletal protein, which may be released into the circulation upon cellular damage as occurs in conditions like intoxications (e. g. hepatic), inflammations (e. g. septic shock), and physical tissue injury (e. g. traffic lesions). Infusion of actin has been demonstrated to cause the formation of thrombi in rats, an effect that could be prevented by preincubation of actin with Gc-globulin (Haddad et al., 1990). In the absence of sufficient Gc-globulin, actin-induced coagulation may lead to subsequent circulatory complications and multiple organ failure. In rats injected actin has been shown to form complexes with Gc-globulin and to be removed primarily by the liver with actin-Gc-globulin complexes being removed faster than actin itself (Harper et al., 1987, Dueland et al., 1991).

Plasma levels of Gc-globulin have been shown to be decreased in patients with liver cirrhosis (Barragry et al., 1978, Walsh and Haddad, 1982, Bouillon et al., 1984, Masuda et al., 1989), hepatic necrosis (Lee et al., 1985, Goldschmidt-Clermont et al., 1988), hepatic acetaminophen (paracetamol) intoxication (Lee et al., 1995, Schiødt et al., 1995), and septic shock (Lee et al., 1989). Decreased levels of free Gc-globulin and increased levels of Gc-globulin-actin complexes can be correlated to survival rate in patients with fulminant hepatic failure (Goldschmidt-Clermont et al., 1988, Lee et al., 1995, Schiødt et al., 1996, 1997, Wians et al., 1997), multiple trauma (Dahl et al., 1998), and septic shock (Lee et al., 1989). In a hamster model of acetaminophen-induced fulminant hepatic necrosis the decreased level of Gc-globulin and increased level of actin-Gc-globulin complexes correlated with the severity of the disease (Lee et al., 1987, Young et al., 1987). Similar observations have been made in rats with experimentally induced septic shock (Watt et al., 1989).

Gc-globulin has not previously been used in medicine, but Yamamoto (1994) has shown that a derivative, Gc-globulin treated with β-galactosidase and sialidase, generates a potent macrophage activating factor and in Yamamoto (1996) a recombinant Gc-globulin is described which is converted into this macrophage activating factor.

Purification of Gc-globulin from human plasma or serum has previously been described by Cleve et al. (1963), Heide and Haupt (1964), Roelcke and Helmbold (1967), Bouillon et al. (1976), Haddad and Walgate (1976), Svasti and Bowman (1978), Chapuis-Cellieretal. (1982), Haddad et al. (1984), Torres et al (1985), Link et al. (1986), Miribel et al. (1986), Taylor et al. (1986) and Swamy et al. (1995). These purifications have all been at an analytical level and are not suited for large-scale production. For example, Chapuis-Cellier et al. (1982) has described a purification procedure for one phenotype of Gc-globulin (Gc1-1) by pseudo-ligand affinity chromatography followed by gel filtration and ion exchange chromatography from 80 ml of human plasma, where the whole process is not suited for a large-scale production. Torres et al (1985) describes an analytical purification procedure for Gc-globulin from serum from one psoriasis patient using a two-step ion exchange displacement chromatography followed by removal of the carboxymethyldextran and further purification on a hydroxyapatite column. Roelcke and Helmbold (1967) describes an analytical purification procedure for Gc-globulin consisting of three column chromatography steps on the same matrix; hydroxyapatite.

Affinity chromatography on vitamin D (Link et al., 1986, Swamy et al., 1995) or actin columns (Haddad et al., 1984), or lengthy procedures including multiple column chromatographic steps have been used. For example, Cleve et al. (1963) used ammonium sulfate precipitation, ion exchange chromatography on TEAE cellulose in phosphate buffer at pH 7.2, preparative starch gel electrophoresis and size exclusion chromatography on Sephadex G-100 to obtain 23 mg Gc-globulin from 1 l human plasma. Heide and Haupt (1964) used multiple ammonium sulfate precipitations, starch gel electrophoresis and size exclusion chromatography to purify Gc-globulin from rivanol-precipitated human plasma fraction IV. Bouillon et al. (1976) used radiolabelled Gc-globulin with radioactive vitamin D in order to be able to follow it during purification and selection of fractions using DEAE cellulose chromatography, ammonium sulfate precipitation, hydroxyapatite chromatography, CM cellulose chromatography, DEAE Sephadex chromatography, repeated hydroxyapatite chromatography, Bio-Gel size exclusion chromatography, and repeated DEAE Sephadex chromatography to obtain 5.2 mg Gc-globulin from 400 ml human serum. Haddad and Walgate (1976) also used radiolabelling with vitamin D to follow Gc-globulin during purification from Cohn fraction IV. The procedure consisted of DEAE cellulose chromatography, size exclusion chromatography on Sephadex G-200, DEAE Sephadex chromatography and preparative polyacrylamide gel electrophoresis. Svasti and Bowman (1978) also used radiolabelling with vitamin D to select fractions for further purification and employed DEAE Sephadex chromatography at pH 8.3, DEAE cellulose chromatography at pH 8.8 and Sephadex G-100 size exclusion chromatography to obtain analytical amounts of Gc-globulin. Chapuis-Cellier et al. (1982) used chromatography on Affigel Blue, Sephadex G-100 size exclusion chromatography, and DEAE-Affigel Blue chromatography to obtain small amounts of Gc-globulin from plasma. Miribel et al. (1986) used sequential chromatography on immobilised Triazine dyes (Cibacron Blue 3-GA followed by DEAELAffigel Blue and finally Fractogel TSK-AF Green) to purify analytical amounts of Gc-globulin. Taylor et al. (1986) used ammonium sulfate precipitation, Blue Sepharose chromatography, DEAE-Sephacel HPLC followed by DEAE 5PW HPLC and finally size exclusion HPLC to purify mg amounts of Gc-globulin. In this procedure radiolabelling with vitamin D was also used to detect Gc-globulin.

In WO97/28688 purification of intracellular vitamin-D binding proteins (IDBPs; which are different from extracellular Gc-globulin) which are used for treating patients with over or under production of vitamin-D or other steroidal hormones. The IDBPs are purified using anion exchange chromatography, hydrophobic interaction chromatography and hydroxyapatite chromatography.

Thus, there is a need for an improved purification large-scale process for production of Gc-globulin and a Gc-globulin medicinal product.

SUMMARY OF THE INVENTION

In this invention, a simple preparative purification process for Gc-globulin from ethanol-precipitated human plasma fraction IV is described. The process gives high yields and Gc-globulin of high purity. Moreover, the process leads to a virus safe Gc-globulin solution, which is ready for use as a medicinal product for intravenous administration.

Thus, the present invention relates to a novel purification process for large-scale production of Gc-globulin. The source of Gc-globulin is preferably a crude plasma fraction but can be any solution, suspension or supernatant containing Gc-globulin, e.g. a milk product, colostrum or a fermentation broth. The Gc-globulin can be plasma-derived or produced by a genetic modified organism. The process of the invention includes two key elements: purification by series of ion exchange chromatography steps, and performing at least two virus-reduction steps. The present invention also discloses the use of Gc-globulin in medicine and the preparation of a Gc-globulin medicinal product. The product can be used in therapy for patients with circulatory disorders and complications, i.e., where it is contemplated that said patients would benefit from the administration of Gc-globulin.

DETAILED DISCLOSURE OF THE INVENTION

The present invention discloses a large scale process for purifying Gc-globulin comprising three or less chromatography steps on ion exchange matrices and one or more validated virus reducing steps, the Gc-Globulin produced by this process, the use of Gc-Globulin for preparing a medicine and a formulation comprising Gc-Globulin.

Gc-globulin can be purified from a wide range of starting materials containing Gc-globulin. In one embodiment, the starting material for the process of the invention is a Gc-globulin-containing supernatant or a lysed cell suspension from a bacterial, fungal, yeast or mammalian cell culture producing Gc-globulin, said cell culture comprising cells coding for mammalian (e.g. human) Gc-globulin. The Gc-globulin-expressing cell culture is grown in a medium providing the cell culture the nutrients needed with or without serum added to the culture medium. In another embodiment, Gc-globulin is purified from milk and/or colostrum from a mammal expressing human Gc-globulin. In one embodiment, the mammal is a transgenic non-human animal.

In a preferred embodiment of the invention, the starting material for the process of the invention is crude plasma, a chromatographically purified plasma fraction, a plasma fraction obtained by ammonium sulfate, polyethylene glycol or caprylic acid precipitation, or a crude plasma protein fraction obtainable from industrial scale ethanol fractionation procedures, such as Cohn fraction I, II, III plus IV; Cohn fraction II, III plus IV; or Cohn fraction III plus IV. In a preferred embodiment, the plasma protein fraction is Cohn fraction IV, where filter aid may or may not be present depending on the method employed for isolation of the Cohn fraction, i.e. by filtration or centrifugation. Each of the starting materials may require a few pre-processing steps to obtain a Gc-globulin-containing solution, which is a protein mixture, where Gc-globulin may constitute less than 1% of the total proteins from the starting materials.

Purification by means of the present invention results in Gc-globulin purified to a very high degree, i.e. more than 100 fold from the starting material. Also, a purification which is 25, 30, 40, 50 or 75 fold is acceptable. Purification to a minor degree is especially acceptable when less complex protein mixtures are used as the starting material. That is, if Gc-globulin constitutes more than 1% of the total protein content.

Purification is achieved by passing the said protein solution through a series of ion exchange columns using conditions of pH, temperature, and ionic strength ensuring that the Gc-globulin will either bind to the column, wherefrom it can subsequently be eluted, or will pass unbound through the column while other, contaminating proteins are retained bound to the column, wherefrom they can subsequently be eluted.

The columns used are ion exchange matrices having either anion exchange properties or cation exchange properties or a mixed bed combination of these. The ion exchange matrices may be selected from a list of commercially available matrices having one or more of the following chemical entities attached diethylaminoethyl (DEAE), quaternary aminoethyl (QAE), quaternary ammonium (Q), carboxymethyl (CM), sulfopropyl (SP), sulfonyl (S) groups. Commercially available matrices are based on agarose, dextran, acrylamide, silica, ceramic materials and other materials, and include DEAE cellulose, DEAE Sepharose, QAE cellulose, QAE Sepharose, Q Sepharose, S Sepharose, SP Sepharose, CM cellulose, CM Sepharose, and several others.

The number of ion exchange columns and the order of these may vary depending on the starting material. In a preferred embodiment, the Gc-globulin solution is first chromatographed on an anion exchange column, then a cation exchange column, and subsequently an anion exchange column. Preferably, the columns are cleaned before and after use with 0.5 M NaOH in order to ensure aseptic production conditions and avoid batch-to-batch contamination. After application of the Gc-globulin-containing solution to a matrix, the column is washed. The buffers used for washing are non-denaturing buffers having a composition, pH, and ionic strength resulting in elimination of a proportion of protein contaminants without substantial elution of Gc-globulin or resulting in recovery of unbound Gc-globulin while leaving a major proportion of contaminating proteins bound to the column.

The pH and composition of the buffers are chosen from knowledge of the isoelectric point and molecular weight of the Gc-globulin and the contaminating proteins. This knowledge may be obtained by isoelectric focusing, capillary electrophoresis, sodium dodecyl sulphate polyacrylamide gel electrophoresis (SDS-PAGE), mass spectrometry, or a combination of these, such as two-dimensional gel electrophoresis.

The buffer can be a Tris buffer, a phosphate buffer, or any other buffer with a suitable buffering capacity, as will be known by persons skilled in the art.

The chromatographic steps of the process of the present invention have several advantages. These comprise, but are not limited to: simplicity, robustness, a high degree of purification, a high recovery/yield, removal of viruses, concentration by volume reduction.

A key element in the present process is the performance of at least two virus-reduction steps, which can be validated. When discussing virus reduction steps, it is understood that a virus reduction step can be either a virus removal step and/or a virus inactivation step. At least two virus removal steps and/or virus inactivation steps may be included in the present process.

The preferred process for production of Gc-globulin from a crude Gc-globulin-containing plasma protein fraction contains the steps outlined below:

Step A) Preparing an Aqueous Suspension from an Ethanol Precipitated Crude Gc-Globulin-Containing Protein Fraction at Substantially Non-Denaturing Temperature and pH.

The term "substantially non-denaturing" implies that the condition to which the term refers does not cause substantial irreversible loss of functional activity of the Gc-globulin molecules, e.g. loss of actin-binding activity, as may be determined by e.g. a crossed immunoelectrophoresis assay, an electrophoretic mobility shift assay, a solid phase binding assay, or a solution phase binding assay. Advantageously, the plasma protein fraction is suspended in water buffered with at least one non-denaturing buffer system at volumes from 5 to 15, preferably from 8 to 12, times that of the plasma protein fraction. The pH of the Gc-globulin-containing suspension is maintained within a pH of 4 to 10, such as within the range 7 to 9, preferably 7.5 to 8.5, most preferably about 8, in order to ensure optimal solubility of the Gc-globulin solution and to ensure conditions compatible with the conditions chosen for the subsequent ion-exchange step. Any suitable buffer can be used, as will be known by persons skilled in the art, but the buffer system preferably contains at least one of the following buffers and bases: sodium dihydrogen phosphate, disodium hydrogen phosphate, Tris (hydroxymethyl)aminomethane, Tris-hydrochloride, NaOH. Persons skilled in the art will appreciate that numerous other buffers can be used. The Gc-globulin-containing suspension is preferably maintained at cold room temperature until the first ion-exchange step, in order to prevent substantial protein denaturation and to minimise protease activity. The Gc-globulin-containing suspension and water as well as the buffer system added preferably have the same temperature within the range of 0 to 12° C., preferably 2 to 10° C., most preferably 3 to 8° C.

The suspension of ethanol-precipitated paste contains large amounts of aggregated protein material. Optionally, the Gc-globulin-containing suspension is filtered in order to remove e.g. large aggregates, filter aid, if present, and residual non-dissolved paste. The filtration is preferably performed by means of depth filters, e.g. C150 AF, AF 2000 or AF 100 (Schenk), 30LA, 50LA or 90LA (Cuno) or similar filters, and delipid filters (Cuno) mounted in a filter press and filter houses. The removal of aggregates, filter aid, if present, and residual non-dissolved protein material could also be carried out by centrifugation. Preferably, a flow-through centrifuge (e.g. Westfalia) is used. The filtered and clarified suspension contains Gc-globulin as a minor component at a relatively low concentration, e.g. 0.5 to 3% of total protein.

Optionally, the recovered, clarified, Gc-globulin-containing solution is concentrated 4 to 6 fold, which can be performed by an ultrafiltration process. The membranes employed for the ultrafiltration advantageously have a nominal weight cut-off within the range of 10,000 to 50,000 Da. A preferred membrane type for the present process is a polysulfone membrane with nominal weight cut-off of 30,000 Da, obtained from Sartorius or Millipore. Other ultrafiltration membranes of comparable material and porosity may be employed. Ultrafiltration can advantageously be followed by diafiltration to exchange the buffer, hereby performing an ultra/diafiltration. The term "ultra/diafiltration" means that the concentration and dialysis by ultrafiltration and diafiltration, respectively, is performed in one step. It is contemplated that the diafiltration and ultrafiltration may be performed as two separate steps. However, in order to prevent unnecessary loss of the product, it is presently preferred to perform the dialysis and concentration by the methods of diafiltration and ultrafiltration in one step. Optionally the concentrated Gc-globulin-containing solution is depth filtered to remove larger particles and aggregates formed by use of 90LA and or 50LA filters (Cuno).

Step B) Ion Exchange Chromatography of the Aqueous Suspension of Gc-Gobulin.

The concentrated and optionally filtered Gc-globulin-containing solution is subjected to at least two steps, but optionally three steps of anion and cation exchange chromatography in order to remove a substantial proportion of the non-Gc-globulin contaminants, e.g. albumin, antitrypsin and other native and denatured proteins. In a preferred embodiment, the concentrated and optionally filtered Gc-globulin-containing solution is applied to an anion exchange resin packed in a column of appropriate dimensions, and the Gc-globulin-containing fraction eluted from the anion exchange resin is applied to a cation exchange resin packed in a column of appropriate dimensions, and the Gc-globulin-containing flow-through fraction from the cation exchange resin to be loaded onto another anion exchange resin packed in a column of appropriate dimensions.

When performing the first ion exchange chromatography step in the purification process of Gc-globulin, it is preferred that the application conditions, e.g. the pH and ionic strength, are chosen in such a way that a major portion of the contaminants about 40% (e.g. non-Gc proteins and aggregates) in the applied solution passes through the column to be non-adsorbed or only weakly retained to be eliminated in the flow-through and/or washing fraction, and substantially all of the Gc-globulin binds to the anion exchange resin together with the remaining protein contaminants. The preferred elution conditions are chosen to result in elution of the Gc-globulin molecules retained by the resin with almost full recovery (94% to 100%) and coelution of a minor portion of the protein contaminants such as 20% bound to the anion exchange resin.

The preferred conditions chosen for performance of the subsequent ion exchange step, e. g. cation exchange chromatography, result in binding of the majority of the non-Gc-globulin molecules present in the solution loaded onto the ion-exchange resin, with collection of the Gc-globulin with almost full recovery (90% to 100%) in the flow-through fraction, with Gc-globulin constituting from 40 to 80% of the total protein content. By this the protein contaminants are removed from the applied material to be eluted from the cation exchange resin during the subsequent cleaning of the column. To reach these conditions, the Gc-globulin-containing fraction eluted from the anion exchange resin is subjected to an ultra/diafiltration process. By this the Gc-globulin-containing fraction is concentrated from 3.5 to 5 fold and the buffer exchanged to that used for equilibration of the cation exchange column. The membranes employed for the ultrafiltration advantageously have a nominal weight cut-off within the range of 10,000 Da to 50,000 Da. A preferred membrane type for the present process is a polysulfone membrane with nominal weight cut-off of 30,000 Da, obtained from Sartorius or Millipore.

Step C) Virus Reduction.

Virus inactivation by solvent detergent (S/D) treatment is preferably performed on the Gc-globulin-containing flow-through fraction recovered from the cation exchange resin after filtration through an 0.45 $\mu$m filter (e.g. Sartorius or Pall). After S/D treatment for at least 6 hours the Gc-globulin-containing flow-through fraction is advantageously diluted with an appropriate amount of a buffer compatible with the equilibration conditions e.g. the pH and ionic strength chosen for the last chromatography step, anion exchange chromatography.

In a preferred embodiment, the optionally diluted S/D-treated Gc-globulin-containing solution is applied to an anion exchange resin packed in a column of appropriate dimensions to retain Gc-globulin on the column and thoroughly wash out the detergent and solvent. The Gc-globulin-containing fraction to be eluted from the anion exchange resin with a high recovery (65 to 85%) is of high purity, i.e. Gc-globulin constituting from 80 to 98% of the total protein content.

Although the preferred embodiment in the process of the present invention includes three ion exchange steps, advantageously an anion exchange chromatography followed by a cation exchange and finally another anion exchange chromatography, it is contemplated that it is also possible to perform the order of the ion exchange steps in the process differently. Instead of performing the ion exchange steps on columns packed with the resin of choice, the ion exchange steps can be performed as batch wise protein adsorption, by adding the resin of choice to the Gc-globulin-containing solution, as will be known by persons skilled in the art of protein purification.

Several reasons make it preferable to perform the anion exchange chromatography before the cation exchange chromatography step. First, the buffer for extraction can have the same composition as the equilibration buffer for the anion chromatography step, meaning that no buffer exchange is necessary. Secondly, the purity of the Gc-globulin-containing fraction obtained by anion exchange chromatography makes it possible to obtain a marked increase in purity by use of a subsequent cation exchange chromatography. To let an anion exchange chromatography be the subsequent step to the combined cation exchange chromatography and S/D treatment step has several advantages. First, there is no need for an intermediary step of a buffer exchange. Adjustment of pH and ionic strength is sufficient. Secondly, the retainment of Gc-globulin applied to the column has two advantages: washing out of the S/D chemicals and a further purification of the Gc-globulin by the following elution from the column. Exchanging the order of the chromatography steps would therefore lead to a more laborious process compared to keeping the order of the ion exchange chromatography steps as proposed in the process of the present invention.

As will be known by persons skilled in the art, ion exchangers may be based on various materials with respect to the matrix as well as to the attached charged groups. For example, the following matrices may be used, in which the materials mentioned may be more or less crosslinked: agarose-based (such as SEPHAROSE CL-6B® matrix, SEPHAROSE FAST FLOW® matrix and SEPHAROSE HIGH PERFORMANCE® matrix), cellulose-based (such as DEAE SEPHACEL® matrix), dextran-based (such as SEPHADEX® matrix), silica-based and synthetic polymer-based. For the anion exchange resin, the charged groups which are covalently attached to the matrix may e.g. be diethylaminoethyl (DEAE), quaternary aminoethyl (QAE), and/or quaternary ammonium (Q). For the cation exchange resin, the charged groups which are covalently attached to the matrix may e.g. be carboxymethyl (CM), sulfopropyl (SP) and/or methyl sulfonate (S). In a preferred embodiment of the present process, the anion exchange resin employed is Q SEPHAROSE FAST FLOW® resin, but other anion exchangers can be used. A preferred cation exchange resin is CM SEPHAROSE FAST FLOW® resin, but other cation exchangers can be used.

The appropriate volume of resin used when packed into an ion exchange chromatography column, reflected by the dimensions of the column i.e. the diameter of the column and height of the resin, varies depending on e.g. the amount of Gc-globulin and protein contaminants in the applied solution and the binding capacity of the resin used.

Before performing an ion exchange chromatography, the ion exchange resin is preferably equilibrated with a buffer which allows the resin to bind its counterions. Preferably, the anion exchange resins are equilibrated with a buffer allowing optimal binding of the Gc-globulin loaded onto the column. Preferably, the cation exchange resin is equilibrated with a buffer allowing optimal binding of the protein contaminants present in the applied Gc-globulin solution without retaining Gc-globulin.

If, for instance, the chosen anion exchange resin for the first step is Q Sepharose FF, then the column is advantageously equilibrated with a non-denaturing neutral to basic buffer having about the same pH and ionic strength as the Gc-globulin solution to be loaded. Any of a variety of buffers is suitable for the equilibration of the ion exchange column, e.g. sodium phosphate or tris(hydroxymethyl)amino-methane. Persons skilled in the art will appreciate that numerous other buffers may be used for the equilibration as long as the pH and conductivity are about the same as for the applied Gc-globulin solution. A preferred buffer for the equilibration of the anion exchange column is a Tris buffer having a Tris concentration within the range of 5 mM to 60 mM, such as within the range of 10 to 30 mM, preferably about 20 to 25 mM. To the buffer a salt is advantageously added, such as sodium chloride in an amount giving a concentration within the range of 10 to 60 mM preferably about 40 to 45 mM. It is preferred that the pH of the Tris buffer used for equilibration is within the range of 7 to 9, such as within the range of 7.5 to 8, preferably about 8. The conductivity is preferably within the range of 3 to 8 mS/cm, most preferably about 5.3 mS/cm. Suitable Tris buffers may be prepared from Tris (hydroxymethyl)aminomethane and/or Tris(hydroxymethyl) aminomethane-hydrochloride, sodium chloride and HCl or NaOH.

Prior to loading the clarified and optionally filtered Gc-globulin-containing solution onto the anion exchange column, the buffer concentration and pH of said solution is preferably adjusted, if necessary, to values substantially equivalent to the concentration and the pH of the employed equilibration buffer.

After loading the Gc-globulin-containing solution onto the column, the column is preferably washed with 5 to 10 column volumes such as 7 to 8 column volumes of a washing buffer in order to remove protein contaminants from the resin with the washing buffer having a pH and ionic strength sufficient to elute a major part of the contaminants from the anion exchange resin without causing substantial elution of Gc-globulin.

The washing is advantageously performed by using the equilibration buffer, even though other buffers, with a similar concentration- and pH-value may be used for the washing. It is preferred that a Tris buffer with NaCl added is used for washing out contaminants from the anion exchange resin. The pH of the buffer could be from 7 to 9, such as within the range of 7.5 to 8.5, such as 8.

The elution of the Gc-globulin from the anion exchange resin is preferably performed with a substantially non-denaturing buffer having a pH and ionic strength sufficient to cause efficient elution of the Gc-globulin with a minimum coelution of protein contaminants, thereby recovering a Gc-globulin-containing eluate. In this context, efficient elution means that at least 75%, such as at least 85%, e.g. at least 95% or more of the Gc-globulin proteins loaded onto the anion exchange resin are eluted from the resin. The elution is advantageously carried out as a step gradient elution with a constant sodium chloride concentration. In the process of the present invention, the preferred buffer used is Tris having a pH within the range of 7 to 9, such as 7.5 to 8.5, preferably about 8 and a concentration within the range of 5 to 60 mM, such as within the range of 10 to 30 mM, preferably about 20 mM.

It is preferred that the salt concentration of the eluting buffer is sufficiently high in order to displace the Gc-globulin from the resin. However, it is contemplated that a decrease in pH and a lower salt concentration can be used to elute the Gc-globulin from the resin. In a preferred embodiment of the present process, the elution is conducted as a step gradient elution with a constant salt concentration eluting Gc-globulin e.g. a sodium chloride concentration within the range from 60 to 150 mM, such as 100 to 120 mM, preferably about 100 mM sodium chloride.

The elution can also be performed by a continuous salt gradient elution. If a continuous salt gradient elution is performed, the concentration of salt may advantageously be within the range from 0 to 150 mM, preferably from about 40 mM to about 100 mM sodium chloride. The advantage of the step gradient elution compared to the continuous salt gradient elution is that the elution is more efficient with a constant salt concentration and the purity of the eluted fraction is higher.

Various other suitable buffer systems may be used for eluting the Gc-globulin, and the elution buffer may further comprise a protein stabilising agent, as will be appreciated by those skilled in the art.

Subsequent to elution from the anion exchange column, the eluate is preferably desalinated (i.e. dialysed) and advantageously concentrated.

The change of buffer and the concentration of Gc-globulin can be performed by a combined ultra/diafiltration process. The term "ultra/diafiltration" means that the dialysis and concentration by diafiltration and ultrafiltration, respectively, is performed in one step. It is contemplated that the diafiltration and ultrafiltration may be performed as two separate steps. However, in order to prevent unnecessary loss of the product, it is presently preferred to perform the dialysis and concentration by the methods of diafiltration and ultrafiltration in one step.

The membranes employed for the dia/ultrafiltration advantageously have a nominal weight cut-off within the range of 10,000 to 50,000 Da. A preferred membrane type for the present process is a polysulfone membrane with nominal weight cut-off of 30,000 Da, obtained from Sartorius. Other ultrafiltration membranes of comparable material and porosity may be employed.

The extent of concentration may vary considerably. The solution is concentrated from about 2 to about 10 fold, such as 3 to 7 fold, preferably about 4 fold that of the starting volume, preferably constituting a final volume from about 0.5 to 3 times that of the cation exchange resin, such as about 1.3 to 1.8 times the resin volume. A preferred buffer for the diafiltration is 15 mM to 25 mM, such as 20 mM sodium phosphate, pH 5.7. The exchange of buffer is continued until the conductivity of the ultrafiltrated solution is reduced to a value less than about 5–6 mS/cm, preferably about 1.5 to 3 mS/cm. During the dia/ultrafiltration, the pH is preferably kept within the range of 5 to 8, preferably 5.4 to 6.5, most preferably at about 5.7.

After dia/ultrafiltration the concentrated solution may be filtered through a filter within the range of 0.2 to 1 $\mu$m, preferably about 0.45 $\mu$m, in order to remove aggregates before the next step.

The appropriate volume of resin used for the cation exchange chromatography column, is reflected by the dimensions of the column (i.e. the diameter of the column and height of the resin), and varies depending on e.g. the amount of protein in the applied solution and the binding capacity of the resin used.

Before performing cation exchange chromatography, the ion exchange resin is preferably equilibrated with a buffer which allows the resin to bind the proteins to be removed from the applied solution. If, for instance, the chosen cation exchange resin is CM Sepharose FF, it is equilibrated with a non-denaturing acidic buffer having about the same pH and ionic strength as the Gc-globulin solution to be loaded. Any of a variety of buffers is suitable for the equilibration of the ion exchange columns, e.g. sodium acetate, sodium phosphate, tris(hydroxymethyl)amino-methane. Persons skilled in the art will appreciate that numerous other buffers may be used for the equilibration as long as the pH and conductivity are about the same as for the applied Gc-globulin solution. A preferred buffer for the equilibration of the cation exchange column is a sodium phosphate buffer having a sodium phosphate concentration within the range of 5–30 mM, such as within the range of 10 to 25 mM, preferably about 20 mM. It is preferred that the pH of the sodium phosphate buffer used for equilibration is within the range of 5.3 to 6.5, such as within the range of 5.4 to 5.9, preferably about 5.7. The conductivity is within the range of 1 to 3 mS/cm, preferably about 1.5 mS/cm. Suitable phosphate buffers may be prepared from disodium hydrogenphosphate and/or sodium dihydrogenphosphate and HCl and/or NaOH.

Prior to loading the ultra/diafiltrated and optionally filtered Gc-globulin-containing solution onto the cation exchange column, the buffer concentration and pH of said solution is preferably adjusted, if necessary, to values substantially equivalent to the concentration and the pH of the employed equilibration buffer.

After loading the Gc-globulin-containing solution onto the cation exchange column, the column is advantageously washed with about 3 to 6 column volumes of a washing buffer in order to ensure that the Gc-globulin is quantitatively washed out from the column to be collected as a combined flow-through/washing fraction appearing as a protein peak on the chromatogram of the UV-signal. The collected fraction constitutes preferably an amount equivalent to about 2 to 3 column volumes. By "quantitatively" is meant that, preferably about 85 to 90% of the Gc-globulin applied to the column, most preferably about 95% or more, is recovered in the Gc-globulin-containing flow-through/washing fraction. Most protein contaminants in the applied material remain advantageously bound to the resin during these preferred conditions. This means that the purity of the Gc-globulin-containing flow-through/washing fraction is relatively high. Preferably, the content of Gc-globulin is within the range from about 40% to 80% of the total protein content.

The washing out of the Gc-globulin from the cation exchange resin is advantageously performed by using the equilibration buffer, even though other substantially non-denaturing buffers having a pH-value and ionic strength sufficient to cause efficient washing out of the Gc-globulin from the cation exchange column leaving most of the contaminants to be retained on the resin may be used for the washing, thereby recovering a Gc-globulin-containing fraction. It is preferred that a phosphate buffer is used for this washing out of the Gc-globulin from the cation exchange resin, the pH of the buffer could be from 5.3 to 6.5, such as within the range of 5.4 to 6.0, such as 5.7. Various other suitable buffer systems may be used for washing out the Gc-globulin, as will be appreciated by those skilled in the art.

Subsequently to the cation exchange chromatography step it is preferred that the washed out Gc-globulin-containing solution is filtered through a filter within the range of 0.2 to 1.0 μm, preferably about 0.45 μm, in order to remove aggregates before the next step.

In the production process of the Gc-globulin product, at least two defined and validated virus removal and inactivation steps are incorporated. These steps are an S/D treatment as a virus-inactivating step towards lipid enveloped viruses and a nanofiltration step preferably to remove small non-enveloped viruses. Besides the stringent requirements for virus safety of the starting plasma material, which are regulated by international guidelines, and the well known virus-reducing capacity of a multistep purification process, the incorporation of two independent virus reduction steps being active against both enveloped and non-enveloped viruses, the medicament of the present invention is substantially virus-safe.

Infectious lipid enveloped viruses that may still be present in the Gc-globulin-containing fraction washed out from the cation exchange column are preferably inactivated at this stage of the process by addition of a virucidal amount of virus-inactivating agent to the said Gc-globulin-containing solution. A "virucidal amount" of virus-inactivating agent is intended to denote an amount giving rise to a solution in which the virus particles are rendered substantially non-infectious and by this a "virus-safe Gc-globulin-containing solution" as defined in the art is obtained. Such "virucidal amount" will depend on the virus-inactivating agent employed as well as the conditions such as incubation time, pH, temperature, content of lipids, and protein concentration.

The term "virus-inactivating agent" is intended to denote such an agent or a method which can be used in order to inactivate lipid enveloped viruses as well as non-lipid enveloped viruses. The term "virus-inactivating agent" is to be understood as encompassing both combinations of such agents and/or methods, whenever that is appropriate, as well as only one type of such agent or method.

Preferred virus-inactivating agents are detergents and/or solvents, most preferably detergent-solvent mixtures. It is to be understood that the virus-inactivating agent optionally is a mixture of one or more detergents with one or more solvents. Solvent/detergent (S/D) treatment is a widely used step for inactivating lipid enveloped viruses (e.g. HIV1 and HIV2, hepatitis type C and non A-B-C, HTLV 1 and 2, the herpes virus family, including CMV and Epstein Barr virus) in blood products. A wide variety of detergents and solvents can be used for virus inactivation. The detergent may be selected from the group consisting of non-ionic and ionic detergents, and is selected to be substantially non-denaturing. Preferably, a non-ionic detergent is used as it facilitates the subsequent elimination of the detergent from the Gc-globulin preparation by the subsequent step. Suitable detergents are described, e.g. by Shanbrom et al., in U.S. Pat. No. 4,314,997, and U.S. Pat. No. 4,315,919. Preferred detergents are those sold under the trademarks TRITON® X-100 detergent and TWEEN® 80 detergent. Preferred solvents for use in virus-inactivating agents are di- or trialkylphosphates as described e.g. by Neurath and Horowitz in U.S. Pat. No. 4,764,369. A preferred solvent is tri(n-butyl)phosphate (TNBP). An especially preferred virus-inactivating agent for the practice of the present invention is a mixture of TNBP and TWEEN® 80 detergent, but, alternatively, other combinations can be used. The preferred mixture is added as a volume such that the concentration of TNBP in the Gc-globulin-containing solution is within the range of 0.2 to 0.6% by weight, preferably at a concentration of about 0.3% by weight. The concentration of TWEEN® 80 detergent in the Gc-globulin-containing solution is within the range of 0.8 to 1.5% by weight, preferably at a concentration of about 1% by weight.

The virus-inactivation step is conducted under conditions that inactivate enveloped viruses resulting in a substantially virus-safe Gc-globulin-containing solution. In general, such conditions include a temperature of 4 to 30° C., such as 19 to 28° C., 23 to 27° C., preferably about 25° C. and an incubation time found to be effective by validation studies. Generally, an incubation time of 1 to 24 hours is sufficient, preferably 4 to 12 hours, such as about 6 hours to ensure sufficient virus inactivation. However, the appropriate conditions (temperature and incubation times) depend on the virus-inactivating agent employed, pH, and the protein concentration and lipid content of the solution.

After the solvent/detergent treatment, the solution is advantageously diluted with buffer to adjust pH and ionic strength. Preferably the concentration and pH of said buffer are of values sufficient to adjust the solution to values substantially equivalent to the concentration, ionic strength and pH of the employed equilibration buffer for the subsequent ion exchange step.

After virus-inactivation ion exchange chromatography is performed in order to remove the virus-inactivating agent and the remaining protein contaminants. This step is preferably performed as already described for the first anion-exchange chromatography step in the present process, with the following two exceptions. First, the volume of the anion exchange resin may be reduced to about 60% that of the anion exchange resin first used and, second, the washing before elution of Gc-globulin is more extensive, at least six to ten column volumes of buffer are used. Additionally, in a preferred embodiment of the invention, the equilibration buffer is sodium phosphate with a concentration within the range of about 5 to 40 mM, preferably 20 mM, and a pH within the range of about 7.5 to 8, preferably 7.8. The buffer is adjusted with sodium chloride preferably to about 20 to 55 mM, preferably 40 mM. The ionic strength of the equilibration buffer is preferable about 4 to 10 mS/cm, preferably 7 mS/cm. As mentioned previously, the sodium phosphate and sodium chloride contents and pH of the Gc-globulin-containing solution is advantageously adjusted to the same concentration and pH as the equilibration buffer.

The preferred method of eliminating the virus-inactivating agent is by ion exchange chromatography. However, other methods, such as oil extraction and alternative chromatographic methods e.g. hydrophobic interaction, are contemplated to be useful. The appropriate method depends on the virus-inactivating agent employed. Removal of solvent/detergent may thus be achieved by binding the Gc-globulin to a resin and, subsequently, a thorough washing out of the inactivating agent with buffer. Anion exchange chromatography is a usable method. In the process of the present invention, anion exchange chromatography is also performed in order to improve the quality and overall purity of the final product of the process. In the preferred embodiment Gc-globulin is eluted from the anion exchange resin with a recovery preferably within the range of 65 to 85%. The purity of the Gc-globulin. containing eluate is preferably about 80% to 95% that of the total protein content, most preferably 98 to 99%.

After the ion exchange chromatography step, the Gc-globulin-containing eluate is preferably dialysed and concentrated; hereby the content of remaining smaller protein components is also effectively reduced. Advantageously, this can be performed by ultra/diafiltration as described previously. The buffer employed for the diafiltration is phosphate buffered saline, PBS, preferably at a concentration of sodium phosphate from 5 to 25 mM, preferably 10 mM, and sodium chloride from about 130 to 160 mM, preferably 150 mM, and at a pH within the range from about 6.5 to 8, preferably about 7.0 to 7.8 such as about 7.4. Alternatively, other physiologically acceptable buffers can be used for the diafiltration as will be known by persons skilled in the art. The diafiltration continues until the osmolality is higher than or equal to 200 mOsm/kg.

Performance of a virus-removing process step results in physical removal of viruses, and this is particularly useful for removal of non-enveloped viruses such as Hepatitis A virus or Parvo virus B19. These are generally not inactivated by the S/D treatment described above.

In a preferred embodiment, the Gc-globulin-containing solution is subjected to filtration through a series of filters allowing Gc-globulin to pass through while retaining virus particles and other infectious particles (e. g. prions). This process may be carried out with different filters having a pore-size distribution preventing particles and viruses with a size larger than the nominal "cut-off" value from passing. These filters may have a cut-off value of 10, 15, 20, 30, 40, 45, 50, 75, 100 nm or another suitable value (nanofilters). Commercially available filters include Planova filters (Asahi), DV filters (Pall) and Viresolve NFP filters (Millipore).

In a preferred embodiment, the Gc-globulin-containing solution is passed through a 35 nm filter (Planova 35N) and then a 15 nm filter (Planova 15N) using a flow-rate and a temperature ensuring optimal performance of the filtration and optimal removal of virus particles, while not exceeding the protein loading capacity of the filters. Preferably the pressure used for filtration is maintained within 0.1 to 1 kg/cm$^2$ and preferably at 0.5 kg/cm$^2$ or lower, and the protein concentration in the solution is adjusted to ensure optimal filtration and recovery of Gc-globulin. The filter area to be used depends on the total volume to be filtered as will be known by persons skilled in the art.

The filters may be used separately or connected in series. Optionally, more than one of each filter may be used either separately or connected in series, e.g. two 35 nm filters and two 15 nm filters, or any other combination resulting in the desired removal of contaminating virus particles. It is understood that other filters with virus-removing properties may also be used, such as depth filters, e.g Zeta Plus VR (Cuno), DV50 and DV20 (Pall), Planova 20N (Asahi) or other filters with the desired properties.

It is contemplated that other methods for removal of or inactivating virus can also be employed to produce a virus-safe Gc-globulin product, such as the addition of methylene blue with subsequent inactivation by radiation with ultra-violet light, as will be known by persons skilled in the art.

If desired, the purified Gc-globulin-containing solution is subjected to further treatments such as addition of stabilising agent for the purpose of making it suitable for formulation as a liquid product to be used, e.g. intravenously, subcutaneously, or intramuscularly.

From a practical point of view it is preferred that the content of the liquid formulation of the Gc-globulin product is the same for storage as for use. The final concentration of Gc-globulin in the product is preferably within the range of 0.1 to 10% by weight (corresponding to 1 g/l to 100 g/l), such as about 0.5 to 10% by weight, i.e. about 0.5%, 1%, 1.5%, 2%, 3%, 4%, 5%, 6%, 7%, 8%, 9%, and 10%.

It is known that a high protein concentration may result in a higher stability of Gc-globulin. On the other hand, a high Gc-globulin concentration means that the maximum infusion rate when administering Gc-globulin intravenously to the patient has to be quite low as side effects, due to the high osmotic pressure of the product, have to be avoided. Presently, there is no recommended concentration for intravenous administration of Gc-globulin advised by the European Pharmacopoeia, however, 0.5% to 5% (w/v) is expected to be advantageous. On the other hand, a quite concentrated product (e.g. 7% or above) is advantageous for intramuscular or subcutaneous injections.

The preferred final formulation of the Gc-globulin product is a compromise between stability and physiologically acceptable conditions with respect to e.g. pH, ionic strength and tonicity.

The closer the pH value is to the physiological pH value i.e. 7.1 to 7.5, preferably 7.2 to 7.4, the higher infusion rate can be employed, depending on the concentration of Gc-globulin.

Furthermore, the Gc-globulin product may comprise protein stabilizing agents. In addition to sugar alcohols and saccharides (such as sorbitol, mannose, glucose, trehalose, maltose), also proteins (such as albumin), amino acids (such as lysine, glycine) and organic agents (such as polyethylene glycol (PEG), caprylic acid, and Tween 80) may be used as well as stabilizers. The suitable concentration of the stabilizing agent in the Gc-globulin-containing solution depends on the specific agent employed as described previously.

The purified Gc-globulin solution is adjusted if necessary in order to obtain a stable and isotonic solution. The term "isotonic solution" is intended to denote that the solution has the same osmotic pressure as in plasma. Mono- or disaccharides may be used to increase the osmolality of the solution since this does not affect the ionic strength. This is preferably performed by addition of sucrose or maltose to a final concentration within the range of about 1% to 10% (w/v), preferably 2% (w/v); other saccharides, such as mannose and glucose, can alternatively be used.

An advantage of the product obtainable by the method of the invention is that, when formulated as a liquid preparation, the product is ready for use and stable.

Although not preferred, it is evident that the product obtained by the various process steps of the invention can also be used as e.g. freeze dried products instead of as liquid formulations, although this is less favourable compared to the use of the product as an instant liquid formulation.

The present invention aims at producing Gc-globulin in large production scale. By "large production scale" is meant, when a crude plasma protein fraction is the starting material, understood that the starting material preferably is a plasma pool from not fewer than 1,000 donors. Alternatively, "large production scale" can be production using genetic modified microorganisms or mammals other than humans from an appropriate large starting volume.

The Gc-globulin product is manufactured according to GMP, under aseptic conditions in classified locations. The process of the invention is thus designed to produce a Gc-globulin product for use in medicine.

The process of the present invention further aims at purifying Gc-globulin from a cell culture supernatant, from a lysed cell suspension, a milk product, or colostrum for subsequent use of the Gc-globulin product as a medicinal product in humans. Hence, the manufacturing process has to comply with requirements stated in directives and guidelines from EEC to medicinal products such as biotechnological/biological products or products derived from human plasma. For guidance on plasma derived medicinal products, see, e.g., CPMP/BWP/269/95 or similar guidelines.

These requirements include, but are not limited to, the restricted use of chemical agents in the purification process as well as in the final product. In the present process Gc-globulin is purified without the addition of protease inhibitors, such as PMSF, or bacteriostatic agents, such as azide and merthiolate. The product is thus totally free from added protease inhibitors and bacteriostatic agents.

It is of major importance for the clinical effect of the Gc-globulin product that the functional activity of Gc-globulin is maintained, i.e. the product is constituted by functionally active Gc-globulin. In this context a functionally active Gc-globulin is defined as a Gc-globulin capable of binding to actin.

Gc-globulin functional activity can be demonstrated in vitro by binding of Gc-globulin to actin in actin-coated ELISA-plates, a rocket immunoelectrophoresis assay or a crossed immunoelectrophoresis assay where Gc-globulin is mixed with actin, or an electrophoretic mobility shift assay. In electrophoretic assays binding of Gc-globulin causes a change in electrophoretic mobility, which can be used to measure binding activity.

Functional activity can be demonstrated in vivo by injecting laboratory animals with actin and Gc-globulin or by provoking release of actin with compounds like paracetamol and subsequently injecting Gc-globulin in order to prevent circulatory disturbances.

The primary indications for the Gc-globulin product are circulatory disorders and complications resulting from release of actin to the blood stream such as may occur in organ (e. g. liver, kidney) intoxications with medicinal products including paracetamol, in physical trauma resulting from wounds, accidents, burns, and other injuries, disseminated intravascular coagulation, and in inflammatory conditions including septic shock syndrome. Administration of Gc-globulin to said patients (e.g. intravenously) is expected to help in clearing actin from the circulation thereby preventing or alleviating harmful effects of actin.

Other indications include congenital or acquired Gc-globulin deficiency and abnormalities of vitamin-D metabolism, as well as vitamin-D intoxication.

The Gc-globulin produced by the purification process described here may also be used for producing a deglycosylated Gc-globulin product to be used as an adjuvant or to be used for inducing antitumor effects by its macrophage activating effect. In this respect the deglycosylated product may be used for treating various cancers, including breast cancer, colon cancer, stomach cancer, lung cancer, skin cancer, and other types of cancer.

EXAMPLES

It is to be understood that the examples described below are illustrative of embodiments of the present process, and the invention is not intended to be so limited.

Example 1

Process Steps in the Purification of Plasma Derived Gc-Globulin to be Used as a Medical Product All steps are performed at room temperature, except for step 5 which is performed at 25±1° C., and steps 1 and 2 which are performed at 5±3° C.

Step 1. Preparation of Cohn Fraction IV Paste.

Cohn fraction IV paste is prepared from human plasma by a standard Cohn fractionation procedure (Cohn et al., 1946) essentially as modified by Kistler and Nitschmann (1952). The ethanol precipitation is initiated after the cryoprecipitate has been removed and, if desired, after adsorption of certain plasma proteins (such as Factor IX and Antithrombin) to e.g. an ion exchange material and/or a Heparin Sepharose matrix. The exact conditions (pH, ethanol concentration, temperature, protein concentration) for obtaining the fraction IV paste appear from the figure at page 266 in Harns JR (ed), Blood Separation and Plasma Fractionation, Wiley-Liss, New York, 1991. The paste is isolated on a filter press by adding filter aid prior to filtration.

Step 2. Extraction of Gc-globulin from Cohn Fraction IV Paste.

From about 37.3 kg of fraction IV paste including filter aid (Schenk, Germany) corresponding to a starting volume of plasma of about 375 kg, extraction is accomplished by first adding 373 kg of 20 mM Tris buffer containing 40 mM sodium chloride, pH 8.0, with slow stirring for about 15 hours. Just before filtration 1.7 kg of filter aid (Celite) is added to the suspension of fraction IV.

The suspension is filtered through a series of depth filters with decreasing pore sizes and a delipid filter: C-150-AF filter plates (Schenk, Germany), and cartridges of 50LA, of 90LA, and of delipid filters (Cuno, France). The filtrated Gc-globulin-containing solution is optionally ultrafiltrated on a system employing membranes with a nominal weight cut-off value of 30 kDa (Sartorius, Germany), by this the solution is concentrated approximately 5 fold.

Step 3. Chromatography on Q Sepharose (Anion Exchange Matrix).

A column is packed with 650 ml of Q Sepharose FF (Amersham Pharmacia Biotech) and equilibrated with 20 mM Tris buffer containing 40 mM sodium chloride, pH 8.0.

A volume of the concentrated Gc-globulin-containing solution from step 2 containing an amount of Gc-globulin of about 1200 mg is applied to the column. Following application the column is washed with 8 column volumes of equilibration buffer to wash out unbound protein contaminants. Subsequently Gc-globulin is eluted from the anion exchange column with 6 column volumes of 20 mM Tris buffer containing 100 mM sodium chloride, pH 8.0, and the eluted Gc-globulin fraction is recovered.

Step 4. Chromatography on CM Sepharose (Cation Exchange Matrix).

The eluted Gc-globulin fraction from step 3 is concentrated 4 fold and desalted by ultra/diafiltration. The employed membrane is a polysulfone membrane with a nominal weight cut-off of 30 kDa (Sartorious). The diafiltration is performed against a buffer of 20 mM sodium phosphate, pH 5.7, and is continued until the pH is 5.7, and the conductivity is 1.5 mS/cm.

A column is packed with 390 ml of CM Sepharose FF (Amersham Pharmacia Biotech) and equilibrated with 20 mM sodium phosphate, pH 5.7. After dia/ultrafiltration the Gc-globulin-containing solution is applied to the column. Gc-globulin passes through the column without binding to the CM Sepharose resin. Following application the column is washed with 3 column volumes of equilibration buffer to wash out all of the unbound Gc-globulin. The Gc-globulin containing flow-through and washing fraction is collected as the Gc-globulin-containing eluate from the cation exchange column.

Step 5. S/D Treatment.

The Gc-globulin-containing eluate from step 4 is filtered through a combined 0.45 μm and 0.2 μm filter (Sartobran P Capsule, Sartorius, Germany). The filtrate is subsequently S/D treated by adding Tween 80 and TNBP to final concentrations of 1.0% and 0.3% by weight, respectively. The S/D treatment proceeds for at least 6 hours at 25° C.

Step 6. Removal of S/D by Anion Exchange Chromatography.

A column is packed with 390 ml of Q Sepharose FF (Amersham Pharmacia Biotech, Sweden) and equilibrated with 20 mM sodium phosphate containing 40 mM NaCl, pH 7.8. The S/D treated Gc-globulin solution is diluted with a volume of 20 mM sodium phosphate containing 48 mM NaCl, pH 9.4, 4 times that of the solution. The diluted Gc-globulin solution is applied to the anion exchange column, the column is subsequently washed with 10 column volumes of equilibration buffer, and Gc-globulin is eluted with 7 column volumes of 20 mM sodium phosphate containing 100 mM NaCl, pH 7.8, and collected.

Step 7. Concentration by Ultrafiltration.

The eluted Gc-globulin fraction is filtered through a combined 0.45 μm and 0.2 μm filter (SARTOBRAN® 300 filter, Sartorius, Germany), and subjected to concentration and exchange of buffer by ultra/diafiltration employing a 30 kDa nominal weight cut-off membranes, first a SARTOCON® slice and subsequently a SARTOCON® Micro UF System (Sartorius, Germany). The concentrated solution containing 10 to 15 mg of Gc-globulin/ml is diafiltrated against PBS, pH 7.3, and finally filtered through a combined 0.45 μm and 0.2 μm filter (MINISART® Plus filter, Sartorius).

Step 8. Nanofiltration and Filling.

The Gc-globulin-containing solution from step 7 is optionally passed through a 35 nm filter (PLANOVA® 35N filter, Asahi) and then a 15 nm filter (PLANOVA® 15N filter, Asahi) without exceeding the protein loading capacity of the filters. The nanofiltration is carried out at room temperature and the pressure used for filtration is maintained at 0.5 kg/cm$^2$ or lower and at least within 0.1–1.0 kg/cm$^2$. The Gc-globulin preparation is sterile filtered (SARTOBRAN® 300 filter, Sartorius), and filled aseptically as 1 g of Gc-globulin per portion in a volume of no more than 100 ml.

Example 2

Validated Virus Reduction Step in the Present Process of Gc-Globulin Purification Virus inactivation by the SD treatment step.

Treatment of the Gc-globulin solution with 1% Tween80+ 0.3% TNBP, at 25° C. for 6 hours has been validated in a study employing PRV (pseudo rabies virus) as a model for a robust enveloped virus. A virus reduction of more than 6.9 $\log_{10}$ was obtained. The result of the validation study shows that the SD treatment step efficiently inactivates enveloped viruses.

Example 3

Analytical Methods to Quantify Gc-Globulin in the Process

Quantitative determination of Gc-globulin by a specific ELISA.

Gc-globulin is quantitated in a Gc-globulin-specific competitive ELISA. Microtiter plates are coated with purified Gc-globulin, washed in blocking buffer (50 mM Tris, pH 7.5, 1% Tween 20, 0.3 M NaCl), and then incubated with samples and mouse monoclonal anti-Gc-globulin antibody. Bound antibodies are detected with alkaline phosphatase-conjugated goat immunoglobulins against mouse immunoglobulins. The alkaline phosphatase converts the colour reagent para-nitrophenyl phosphate in a concentration-dependent manner. The concentration of the samples analysed are estimated by use of a Gc-globulin standard.

Quantitative Determination of Gc-globulin by Rocket Immunoelectrophoresis.

Samples are loaded in wells punched in 1% agarose gels, cast and run in a Tris-barbituric acid-lactic acid buffer, pH 8.6, and containing rabbit immunoglobulins against Gc-globulin (1:40 dilution). Electrophoresis is carried out at 2 V/cm and immune complexes detected by staining with Coomassie Brilliant Blue. The concentration of Gc-globulin in samples is determined by comparison with a Gc-globulin standard.

Determination of Actin Binding by Crossed Immunoelectrophoresis.

Samples are mixed with an excess of actin and subjected to electrophoresis in 1% agarose gels, cast and run in Tris-barbituric acid-lactic acid buffer, pH 8.6. Lanes are cut out and subjected to second dimension electrophoresis as described above under Gc-globulin rocket immunoelectrophoresis. The mobility of the Gc-globulin-actin complex is faster than that of Gc-globulin. The degree of actin-binding Gc-globulin in the sample is determined by measuring the area of the Gc-globulin-actin complex immunoprecipitate and that of the free Gc-globulin and calculating the ratio. The result of this analysis show that Gc-globulin purified by the present process retains 100% actin binding activity.

Example 4

Yield from the Purification Process

The volume of the Gc-globulin containing solution prepared from 37.3 kg of paste IV makes a total of about 360 kg, with a concentration of about 120 mg of Gc-globulin per litre. The Gc-globulin-containing solution is concentrated approximately 5 fold by ultrafiltration employing a membrane with a cut-off value of 30 kDa in order to have a volume easier to handle in the subsequent purification process. The final concentrated Gc-globulin-containing solution with a mean volume of 72 kg, contains about 21 g of total protein and has a mean concentration of 630 mg of Gc-globulin per litre (kg=1).The total recovery from the extraction process results in about 45 g of Gc-globulin, equivalent to 120 mg per kg of starting plasma and 1.2 g Gc-globulin per kg of paste IV.

The concentrated Gc-globulin-containing solution constitutes the material for the subsequent purification steps of the process starting with an anion exchange chromatography step by loading a volume of the solution containing about 1200 mg of Gc-globulin (Example 1). The yield of the purification process is about 835 mg of Gc-globulin corresponding to a recovery of about 70% of the Gc-globulin present in the solution used and a purification factor of 33 relative to the starting extract and 246 relative to plasma. The purity of the final preparation is high, Gc-globulin constitutes about 91% of the total protein content.

Example 5

Gc-Globulin Preparation for Therapeutic Use for IgA Deficient Patients

When using a Cohn fraction IV as the starting material for the purification, the final Gc-globulin preparation can contain IgA in an amount up to 10% of the Gc-globulin content. It is known that IgA deficiency is rather common, with a prevalence of about 1.25 per thousands, and that intravenous injection of IgA might result in serious side effects such as anaphylactic reactions. Very high purity Gc-globulin with only trace amounts of IgA, no more than 0.1%, can be obtained by performing a size exclusion chromatography step after the purification process of the present invention, hereby increasing the safety of a Gc-globulin product for therapeutic use.

Before the size exclusion chromatography is performed the Gc-globulin preparation eluted from the second Q Sepharose column is heavily concentrated by ultrafiltration by employing a membrane with a nominal weight cut-off within the range of 10,000–50,000 Da. A preferred membrane type is a polysulfone membrane with a cut-off of 30,000 Da, obtained from Sartorious or Millipore.

The concentrated Gc-globulin preparation is loaded on a column packed with a size exclusion resin, such as Superdex 200 Prep Grad (Amersham Pharmacia Biotech) and equilibrated with PBS, pH 7.3. The size exclusion chromatography serves two purposes, a purification and a buffer exchange step.

The loaded material may constitute a volume equal to 3% of the packed column volume. IgA and Gc-globulin elute as separate protein peaks, and material eluting as the Gc-globulin peak is collected as the final very high purity Gc-globulin preparation.

Persons skilled in the art of protein purification will find that other resins possessing the ability to separate IgA from Gc-globulin can be used for the size exclusion chromatography. Furthermore other physiological acceptable buffers can exchange PBS for the size exclusion chromatography.

This essentially IgA depleted Gc-globulin preparation can easily be filtered through a nanofilter before formulation as a final Gc-globulin product.

Example 6

Diagnostic Methods to Quantify Gc-Globulin— Both Total Concentration and Unbound/Complexed Gc-Globulin The total concentration of Gc globulin, and the amount of free and actin-bound Gc globulin in blood-samples from patients, is measured using a solid phase competitive ELISA assay, and crossed immuno-electrophoresis, respectively. The blood-sample is centrifuged, and the serum is collected for the analysis. For quantitative determination of total Gc globulin concentration, microtiter plates are coated with purified human Gc-globulin, blocked with buffer (50 mM Tris, pH 7.5, 1% Tween 20, 0.3 M NaCl), followed by incubation with dilutions of patient sera and monoclonal antibody against human Gc globulin. Solis phase bound antibodies are detected using alkaline phosphatase-conjugated goat immunoglobulins against mouse immunoglobulins, followed by para-nitrophenyl phosphate colour-development. The total concentration of Gc globulin in the serum can be estimated from a Gc globulin standard. To estimate the ratio of free and actin-complexed Gc globulin, the serum is further analysed by crossed immuno-electrophoresis. The serum is subjected to first dimension electrophoresis in 1% agarose gels, cast and run in Tris-tricine buffer, pH 8.6. Lanes are cut out and subjected to second dimension electrophoresis in 1% agarose gels containing rabbit immunoglobulins raised against denatured human Gc-globulin (with specificity for both native and denatured Gc globulin; 1:100 dilution). Electrophoresis is carried out at 2 V/cm overnight, and immunoprecipitates detected by Coomassie Brilliant Blue staining. The mobility of actin-complexed Gc globulin is faster than free Gc globulin, resulting in two immunoprecipitates. The degree of complexed versus free Gc globulin in the serum is determined by measuring the area under the two precipitates. (The crossed immuno-electrophoresis can either be used in combination with a Gc globulin standard to calculate the Gc globulin directly, or the assay can give %-values of free/bound Gc globulin, which by comparison to the solid phase concentration determination can be used to estimate the free/bound Gc globulin concentration.

References

Baelen H V, Bouillon R, De Moor P. Vitamin D-binding protein (Gc-globulin) binds actin. J Biol Chem. 1980;255:2270–2.

Barragry J M, Corless D, Auton J, Carter N D, Long R G, Maxwell J D, Switala S. Plasma vitamin D-binding globulin in vitamin D deficiency, pregnancy and chronic liver disease. Clin Chim Acta. 1978;87:359–65.

Bouillon R, Van Baelen H, Rombauts W, De Moor P. The purification and characterisation of the human-serum binding protein for the 25-hydoxycolecalciferol (transcalciferin). Identity with group-specific component. Eur J Biochem. 1976;66:285–91.

Bouillon R, Auwerx J, Dekeyser L, Fevery J, Lissens W, De Moor P. Serum vitamin D metabolites and their binding protein in patients with liver cirrhosis. J Clin Endocrinol Metab. 1984;59:86–9.

Chapuis-Cellier C, Gianazza E, Arnaud P. Interaction of group-specific component (vitamin D-binding protein) with immobilized Cibacron blue F3-GA. Biochim Biophys Acta. 1982;709:353–7.

Cleve H, Prunier J H, Bearn A G. Isolation and characterisation of the two principal inherited group-specific components of human serum. J Exp Med. 1963;118:711–26.

Cohn E J, Strong L E, Hughes W L, Mulford D J, Ashworth J N, Melin M, Taylor H L. Preparation and properties of serum and plasma proteins. IV. A system for the separation into fractions of the protein and lipoprotein components of biological tissues and fluids. J Am Chem Soc. 1946;68: 459–475.

Cooke N E, David E V. Serum vitamin D-binding protein is a third member of the albumin and alpha fetoprotein gene family. J Clin Invest. 1985;76:2420–4.

Dahl B, Schiodt F V, Kiaer T, Ott P, Bondesen S, Tygstrup N. Serum Gc-globulin in the early course of multiple trauma. Crit Care Med. 1998;26:285–9.

Dueland S, Nenseter M S, Drevon C A. Uptake and degradation of filamentous actin and vitamin D-binding protein in the rat. Biochem J. 1991;274:237–41.

Goldschmidt-Clermont P J, Lee W M, Galbraith R M. Proportion of circulating Gc (vitamin D-binding protein) in complexed form: relation to clinical outcome in fulminant hepatic necrosis. Gastroenterology. 1988;94:1454–8.

Haddad J G Jr, Walgate J. 25-Hydroxyvitamin D transport in human plasma. Isolation and partial characterization of calcifidiol-binding protein. J Biol Chem. 1976;251:4803–9.

Haddad J G, Kowalski M A, Sanger J W. Actin affinity chromatography in the purification of human, avian and other mammalian plasma proteins binding vitamin D and its metabolites (Gc globulins). Biochem J. 1984;218:805–10.

Haddad J G, Harper K D, Guoth M, Pietra G G, Sanger J W. Angiopathic consequences of saturating the plasma scavenger system for actin. Proc Natl Acad Sci USA. 1990;87:1381–5.

Haddad J G. Plasma vitamin D-binding protein (Gc-globulin): multiple tasks. J Steroid Biochem Mol Biol. 1995;53:579–82.

Harper K D, McLeod J F, Kowalski M A, Haddad J G. Vitamin D binding protein sequesters monomeric actin in the circulation of the rat. J Clin Invest. 1987;79:1365–70.

Heide K, Haupt H. Darstellung noch nicht therapeutisch angewandter Plasmaproteine. Behringwerk Mitteilungen 1964;43:161–93.

Kawakami M, Blum C B, Ramakrishnan R, Dell R B, Goodman D S. Turnover of the plasma binding protein for vitamin D and its metabolites in normal human subjects. J Clin Endocrinol Metab. 1981;53:1110–6.

Kistler P, Nitschmann H. Large scale production of human plasma fractions. Vox Sang. 1962;7:414–424.

Lee W M, Emerson D L, Young W O, Goldschmidt-Clermont P J, Jollow D J, Galbraith R M. Diminished serum Gc (vitamin D-binding protein) levels and increased Gc:G-actin complexes in a hamster model of fulminant hepatic necrosis. Hepatology. 1987;7:825–30.

Lee W M, Reines D, Watt G H, Cook J A, Wise W C, Halushka P V, Galbraith R M. Alterations in Gc levels and complexing in septic shock. Circ Shock. 1989;28:249–55.

Lee W M, Galbraith R M. The extracellular actin-scavenger system and actin toxicity. N Engl J Med. 1992;326:1335–41.

Lee W M, Galbraith R M, Watt G H, Hughes R D, McIntire D D, Hoffman B J, Williams R. Predicting survival in fulminant hepatic failure using serum Gc protein concentrations. Hepatology. 1995;21:101–5.

Link R P, Perlman K L, Pierce E A, Schnoes H K, DeLuca H F. Purification of human serum vitamin D-binding protein by 25-hydroxyvitamin D3-Sepharose chromatography. Anal Biochem. 1986;157:262–9.

Miribel L, Goldschmidt-Clermont P, Galbraith R M, Arnaud P. Rapid purification of native group-specific component (vitamin D-binding protein) by differential affinity for immobilized triazine dyes. J Chromatogr. 1986;363:448–55.

Roelcke D, Helmbold W., Gc-Darstellung mittels hydroxylapatit-saulen-chromatographie, Blut, 1967, 14:331–340.

Schiodt F V, Bondesen S, Tygstrup N. Serial measurements of serum Gc-globulin in acetaminophen intoxication. Eur J Gastroenterol Hepatol. 1995;7:635–40.

Schiodt F V, Bondesen S, Petersen I, Dalhoff K, Ott P, Tygstrup N. Admission levels of serum Gc-globulin: predictive value in fulminant hepatic failure. Hepatology. 1996;23:713–8.

Schiodt F V, Ott P, Bondesen S, Tygstrup N. Reduced serum Gc-globulin concentrations in patients with fulminant hepatic failure: association with multiple organ failure. Crit Care Med. 1997;25:1366–70.

Svasti J, Bowman B H. Human group-specific component. Changes in electrophoretic mobility resulting from vitamin D binding and from neuraminidase digestion. J Biol Chem. 1978;253:4188–94.

Swamy N, Roy A, Chang R, Brisson M, Ray R. Affinity purification of human plasma vitamin D-binding protein. Protein Expr Purif. 1995;6:185–8.

Taylor G A, Mazhindu H N, Findlay J B, Peacock M. Purification of vitamin D binding protein from human plasma using high performance liquid chromatography. Clin Chim Acta. 1986;155:31–41.

Torres A R, Krueger G G, Peterson E A. Purification of Gc2 globulin b from human serum. Ana.Chem. 1985, 144:469–476.

Walsh P G, Haddad J G. "Rocket" immunoelectrophoresis assay of vitamin D-binding protein (Gc globulin) in human serum. Clin Chem. 1982;28:1781–3.

Wians F H, Lin W, Brown L P, Schiodt F V, Lee W M. Immunonephelometric quantification of group-specific component protein in patients with acute liver failure. Liver Transpl Surg. 1997;3:28–33.

Yamamoto, N. (1994), U.S. Pat. No. 5,326,749.

Yamamoto, N. (1996), WO 9640903.

What is claimed is:

1. A purified Gc-globulin product obtained by a process for large-scale purification of Gc-globulin comprising the steps of ion exchange chromatography and ultra- and/or diafiltration.

2. A preparation comprising Gc-globulin according to claim 1.

3. The preparation according to claim 2, which is a liquid product.

4. The preparation according to claim 2, wherein the preparation further comprises a stabilizing agent.

5. The preparation according to claim 4, wherein the stabilizing agent is selected from the group consisting of sugar alcohols, saccharides, proteins, amino acids, and organic agents.

6. The preparation according to claim 2 comprising an isotonic solution.

* * * * *